(12) United States Patent
Deng et al.

(10) Patent No.: US 7,220,869 B2
(45) Date of Patent: May 22, 2007

(54) BRøNSTED ACIDIC ROOM TEMPERATURE IONIC LIQUIDS EACH HAVING A N-PROTONATED LACTAM CATION AND METHOD FOR PREPARING THE SAME

(75) Inventors: Youquan Deng, Lanzhou (CN); Zhengyin Du, Lanzhou (CN); Shu Guo, Lanzhou (CN); Zuopeng Li, Lanzhou (CN); Laiying Zhu, Lanzhou (CN)

(73) Assignee: Lanzhou Institute of Chemical Physics Chinese Academy of Sciences, Gansu (CN)

( * ) Notice: Subject to any disclaimer, the term of this patent is extended or adjusted under 35 U.S.C. 154(b) by 154 days.

(21) Appl. No.: 11/185,692

(22) Filed: Jul. 21, 2005

(65) Prior Publication Data
US 2007/0021604 A1    Jan. 25, 2007

(30) Foreign Application Priority Data
Nov. 12, 2004   (CN)   ......................... 2004 1 0092789

(51) Int. Cl.
C07D 207/02 (2006.01)
C07D 211/02 (2006.01)
C07D 223/10 (2006.01)

(52) U.S. Cl. ................... 548/543; 546/243; 540/485
(58) Field of Classification Search ................ 548/543; 546/243; 540/485
See application file for complete search history.

(56) References Cited

U.S. PATENT DOCUMENTS

2006/0211871 A1 * 9/2006 Dai et al. ................... 549/208

* cited by examiner

*Primary Examiner*—Kamal A. Saeed
*Assistant Examiner*—Michael P. Barker
(74) *Attorney, Agent, or Firm*—Sughrue Mion, PLLC

(57) ABSTRACT

The invention relates to a class of novel Brønsted acidic ionic liquids each having a lactam cation, and to a method for preparing the same through simple neutralization reaction of a lactam, which is available in large scale from industry, with a Brønsted inorganic or organic acid under room temperature. The properties of the lactam Brønsted acidic ionic liquids are as follows: they are water- and moisture-stable; they are more environmentally benign and lower cost than that of dialkylimidazolium salts; they have stronger Brønsted acidity and can be used as acidic catalysts and media instead of inorganic corrosive acids, such as concentrated sulfuric acid and hydrofluoric acid, in many acid-catalyzed reactions; and they can also be used as green media for extraction and separation.

6 Claims, No Drawings

BRøNSTED ACIDIC ROOM TEMPERATURE IONIC LIQUIDS EACH HAVING A N-PROTONATED LACTAM CATION AND METHOD FOR PREPARING THE SAME

BACKGROUND OF THE INVENTION

1. Field of the Invention

The invention relates to a class of novel Brønsted acidic ionic liquids each having a N-protonated lactam cation and to a method for preparing the same.

2. Description of the Related Art

Room temperature ionic liquids (RTILs) are molten salts with a melting point at or below 100° C., which are generally composed of an asymmetric organic cation, and an inorganic or organic anion. (P. Wasserscheid, T. Welton, Ionic liquids in Synthesis, Wiley-VCH, 2003). In comparison with solid materials, RTILs are liquid; in comparison with conventional liquid materials, RTILs are completely composed of ions. Therefore, RTILs always exhibit specific physicochemical properties and functions that conventional solid or liquid materials are not possessed of. RTILs possess many characteristics, such as nonvolatile or 'zero' vapour pressure, for which RTILs are regarded as green solvents; low melting point (can be lower than about 90° C.); wide liquid range (can be wider than 200° C. or above) and strong electrostatic field, which is a typical characteristics distinguished from molecular media and materials; wide electrochemical window (can be wider than 5V), which means that RTILs show no electrochemical reactions within such wide voltage range, i.e. degradation; good ionic conductivity (up to $2.5 \times 10^{-2}$ S/cm) and thermal conductivity; high heat capacity and heat storage density (6.4 times higher than that of heat storage oil used at present, the heat storage density of the heat storage oil is 9.4 MJ/m$^3$); high thermal stability (decomposition temperature can be up to 400° C.); selective dissolubility, which made RTILs be called "liquid zeolite", and designability. These specific characteristics make RTILs could be "solid liquid" accompanied with characteristics of liquids and solids simultaneously. Theoretically, there are more than several million billion ionic liquids which could be prepared. The combinations of the ionic liquids diversity and their varied functions and characteristics make it possible to synthesize a great deal of functional media and materials having different properties and applications.

In 1948, U.S. Pat. Nos. 4,446,331, 4,446,349, and 4,446,350 disclosed ethylpyridinium halide-aluminium trichloride room temperature ionic liquids which could be used in plating. This can be regarded as the first generation of ionic liquids. However, these RTILs are moisture and air sensitive and are liable to decompose when mixed with water. In 1990s, more stable RTILs each composed of a dialkylimidazolium cation and a anion of BF$_4^-$ or PF$_6^-$ were successfully prepared, which emblematized the naissance of the second generation of ionic liquids (Wilkes J S et al, Air and Water Stable 1-ethyl-3-methylimidazolium Based Ionic Liquids. J. Chem. Soc., Chem. Commun., 1992, 965–967). Due to suitable chemical structure and ideal physicochemical properties of dialkylimidazolium cation, these ionic liquids based on imidazolium have been studied extensively for many years up to the present.

The types and functions of ionic liquids based on imidazolium have been further enriched since 2000 by introducing functional group to the side chain of cations, and a series of task-specific ionic liquids have been prepared, which have endowed these ionic liquids with special properties, functions and applications (A. Wierzbicki, et al, Proceedings of the Symposium on Advances in Solvent Selection and Substitution for Extraction, Atlanta, Ga., Mar. 5–9, 2000). For example, dialkylimidazolium ionic liquids containing an amino group at the end of side chain can trap carbon dioxide at room temperature and release it under high temperature, which could be applied for selective separation of carbon dioxide from gases mixture (Eleanor D. Bates et al, J. Am. Chem. Soc., 2002, 124, 927); dialkylimidazolium ionic liquids each having an urea or thiourea group can coordinate $Cd^{2+}$ and $Hg^{2+}$ selectively to achieve extraction and separation from the solutions (Ann E. Visser et al, Environ. Sci. Technol., 2002, 36, 2523–2529); dialkylimidazolium ionic liquids each having a strong Brønsted acidic group such as —SO$_3$H have been used as catalyst and/or reaction medium in olefin oligomerization (Yanlong Gu et al, Catalysis Communications, 2004, 4, 597), etherification (Amanda C. Cole et al, J. Am. Chem. Soc., 2002, 124, 5962), esterification (Amanda C. Cole et al, J. Am. Chem. Soc., 2002, 124, 5962; Yanlong Gu et al, Journal of Molecular Catalysis A: Chemical, 2004, 212, 71; Jianzhou Gui et al, Catalysis Communications 2004, 5, 473), pinacol rearrangement (Amanda C. Cole, et al, J. Am. Chem. Soc., 2002, 124, 5962), Friedel-Crafts alkylation (Kun Qiao et al, Chemistry Letters, 2004, 33, 472) and Arene nitration (Kun Qiao, et al, Chemistry Letters, 2004, 33, 808). Recently, N-protonated Brønsted acidic ionic liquids based on methylimidazolium were also reported in a number of patents and literatures and could be used as novel liquid acidic catalysts in many acid-catalyzed reactions for replacing conventional inorganic acids, such as sulfuric acid, hydrofluoric acid etc. (Hai-Hong Wu, et al, Tetrahedron Letters, 2004, 45, 4963; Hua-Ping Zhu et al, Green Chemistry, 2003, 5, 38). These ionic liquids can be regarded as the third generation of ionic liquids.

Although dialkylimidazolium cation is quite suitable for constructing ionic liquids, a methylimidazole as a precursor thereof is expensive and available only in small scale because they have not been produced in large scale yet. Furthermore, the environmental compatibility of this kind of ionic liquids has been questioned because the toxicity of dialkylmethylimidazole cation is not so weak. So, the development of a new kind of cheaper and environmentally benign chemical feedstock with specific physicochemical properties as a precursor of cation of RTILs is of great scientific investigation value and practical significance.

Lactam and its derivates are amine derivatives that could be quaternized to act as a new kind of cation of RTILs. There is a carbonyl group in lactam molecules, and this may result in specific physicochemical properties and functions if they are incorporated as a cation into a RTIL. In comparison with conventional pyridines or alkylimidazoles, lactams and derivates thereof may intrinsically lower toxicity, and some lactams such as caprolactam have been produced currently in terms of megatons per year in chemical industry and is costed reasonably lower.

In 2002, it is reported that N-vinyl-N-alkylbutyrolactam ionic liquids through two-step reactions was prepared (D. Demberelnyamba et al, Chem. Commun., 2002, 1538). But these ionic liquids are generally neutral. So far, Brønsted acidic ionic liquids having N-protonated lactam cations have not been reported yet.

DISCLOSURE OF THE INVENTION

This invention presents a class of novel Brønsted acidic ionic liquids containing N-protonated lactam cations and a method for preparing the same.

In an embodiment of the invention, the invention is a Brønsted acidic room temperature ionic liquid having a N-protonated lactam as the cation group, represented by a general formula (I),

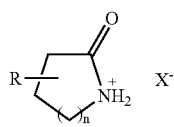

(I)

wherein R represents a hydrogen atom or an alkyl group containing 1 to 4 carbon atoms, n is 1 to 5, and $X^-$ represents the anion group of Brønsted acid HX.

Preferable R is selected from the group consisting of methyl, ethyl, n-propyl, i-propyl, n-butyl, i-butyl and hydrogen atom.

Preferable $X^-$ is selected from of the group consisting of $BF_4^-$, $CF_3SO_3^-$, $CF_3COO^-$, $CH_3COO^-$, $ClCH_2COO^-$, $C_6H_5COO^-$, $C_6H_5CH_2COO^-$, $NO_3^-$, $HSO_4^-$, $H_2PO_4^-$, $(CN)_2N^-$ and $CH_3SO_3^-$.

The representative examples of the Brønsted acidic room temperature ionic liquids each having a N-protonated lactam cations of the invention are:

(1) N-protonated caprolactam tetrafluoroborate

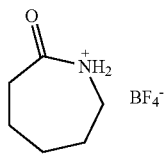

which has a density of 1.34 g/ml (18° C.), no distinct melting point and freezing point, a glass transition temperature of −68.0° C., a kinetic viscosity of 28 cP (25° C.), an electrochemical window of 2.0V, an ionic conductivity of $5.6 \times 10^{-4}$ S/cm (15° C.), and a Hammett acidic scale $H_0 = -0.22$ (using 2,4-dinitroaniline as indicator).

(2) N-protonated caprolactam trifluoroacetate

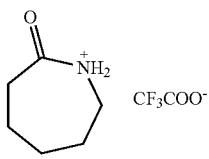

which has a density of 1.26 g/ml (18° C.), no distinct melting point and freezing point, a glass transition temperature of −78.2° C., a kinetic viscosity of 503 cP (25° C.), an electrochemical window of 1.9V, an ionic conductivity of $1.17 \times 10^{-4}$ S/cm (15° C.), and a Hammett acidic scale $H_0 = 4.54$ (using methyl yellow as indicator).

In another embodiment of the invention, the invention is a method for preparing a Brønsted acidic room temperature ionic liquid having a N-protonated lactam as the cation group, represented by a general formula (I),

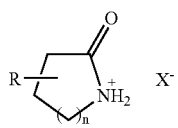

(I)

wherein R represents a hydrogen atom or an alkyl group containing 1 to 4 carbon atoms, n is 1 to 5, and $X^-$ represents the anion group of Brønsted acid HX, characterized by reacting a lactam compound represented by a general formula (II),

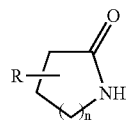

(II)

wherein R represents a hydrogen atom or an alkyl group containing 1 to 4 carbon atoms, and n is 1 to 5, with a Brønsted acid HX at room temperature, in the presence of a reaction medium selected from the group consisting of benzene, toluene, ethyl ether, cyclohexane, water and a mixture thereof.

The molar ratio of the lactam compound to the Brønsted acid HX is 1:1.

The Brønsted acid is selected from the group consisting of tetrafluoroboric acid ($HBF_4$), trifluoromethanesulfonic acid ($CF_3SO_3H$), trifluoroacetic acid ($CF_3COOH$), acetic acid ($CH_3COOH$), chloroacetic acid ($ClCH_2COOH$), benzoic acid ($C_6H_5COOH$), phenylacetic acid ($C_6H_5CH_2COOH$), nitric acid ($HNO_3$), Sulfuric acid ($H_2SO_4$), phosphoric acid ($H_3PO_4$), dicyanoimide ($HN(CN)_2$) and methanesulfonic acid ($CH_3SO_3H$).

The Brønsted acidic room temperature ionic liquids having N-protonated lactam cation in the invention have been characterized and identified by using infrared spectrometer (IR), $^1H$ nuclear magnetic resonance spectroscopy ($^1H$-NMR), $^{13}C$ nuclear magnetic resonance spectroscopy ($^{13}C$-NMR), mass spectroscopy (MS) and elemental analysis. The Melting point was determined with microscopic melting-point-meter for solid samples and with Differential Scanning Calorimeter DSC Q100 available from TA Company for liquid samples. The density of each ionic liquid was determined by gravimetric analysis at 18° C. The data of electrochemical window were measured by using CHI660 electrochemical station. The Kinetic viscosity was measured by using a capillary viscometer at 25° C. in constant-temperature bath. The ionic conductivity was measured by using digital conductivity-meter avaible from Shanghai Scientific Instruments Ltd. The Hammett acidic scale $H_0$ was measured by using Agilent 8453 UV-vis spectrometer with 2,4-dinitroaniline or methyl yellow as indicator.

The Brønsted acidic room temperature ionic liquids having a N-protonated lactam in the invention are moisture- and water-stable, have comparatively strong Brønsted acidity and have widely practical applications. For example, they could be used as acidic catalysts and media instead of inorganic corrosive acid, such as concentrated sulfuric acid, hydrofluoric acid, etc. in many acid-catalyzed reactions. They could also be used as versatile medium for extraction and separation.

In comparison with diakylimidazolium RTILs, the Brønsted acidic room temperature ionic liquids each having a N-protonated lactam cation and method for preparing the same of the invention have the following features:

(1) The raw material cost for the ionic liquids is lower since the lactam and its derivates are much cheaper than that of methylimidazole and its derivates;

(2) The RTILs of the invention are more environmentally benign;

(3) The RTILs of the invention have comparatively strong Brønsted acidity but different physicochemical properties from those conventional ionic liquids based on imidazolium;

(4) The method of the invention is a one-step acid-base neutralized reaction, and also an atom economic reaction with a complete conversion and a high yield, thus making the method environmentally friendly and reducing the preparing cost of the ionic liquids;

(5) The method of the invention could be enlarged to an industrial scale.

EXAMPLES

The invention is further illustrated by the following examples, but not limited within these examples.

Example 1

Preparation of 2-Pyrrolidonium Tetrafluoroborate

To a 100 ml flask containing 8.51 g of 2-pyrrolidone (0.1 mol), 30 ml water was added and stirred for dissolution. Then 21.95 g 40% aqueous solution of tetrafluoroboric acid (0.1 mol) was added dropwise into the flask over 20 min at room temperature. Then the reaction was stirred for another 1 hour. Desired product was formed after water was removed under reduced pressure and then dried at 110° C. under 1–5 mmHg for 1 hour. The brown viscous, moisture- and water-stable liquid of 2-pyrrolidonium tetrafluoroborate was obtained with a yield of 97.2%, which has a glass transition temperature of −73° C., density of 1.46 g/ml, viscosity of 350 cP, an electrochemical window of 2.2 V, an ionic conductivity of $8.39 \times 10^{-4}$ S/cm, and a Hammett acidic scale $H_0$ of 0.91 using 2,4-dinitroaniline as indicator. No melting point was observed.

IR (cm$^{-1}$): 3249, 2953, 2896, 1685, 1290. $^1$H-NMR (400 MHz, CDCl$_3$): 2.29–2.47 (m, 2H), 2.92 (t, J=8.0, 2H), 3.76 (t, J=7.6, 2H), 8.79(s, 1H). $^{13}$C-NMR (100 MHz, CDCl$_3$): 27.83, 36.65, 42.91, 162.93. FAB-MS for cation: m/z 86.2. C$_4$H$_8$BF$_4$NO (172.92): calcd: C, 27.76, H 4.63. Found: C, 27.70, H 4.52.

Example 2

Preparation of Caprolactam Tetrafluoroborate

To a 100 ml flask containing 11.32 g of ε-caprolactam (0.1 mol), 30 ml water was added and stirred for dissolution. Then 21.95 g 40% aqueous solution of tetrafluoroboric acid (0.1 mol) was added dropwise into the flask over 20 min at room temperature. Then the reaction was stirred for another 1 hour. Desired product was formed after water was removed under reduced pressure and then dried at 110° C. under 1–5 mmHg for 1 hour. The yellowish, moisture- and water-stable liquid of N-protonated caprolactam tetrafluoroborate was obtained with a yield of 98.0%, which has a glass transition temperature of −78.2° C., a density of 1.34 g/ml, a viscosity of 503 cP, an electrochemical window of 2.0V, an ionic conductivity of $5.6 \times 10^{-4}$ S/cm, and a Hammett acidic scale $H_0$ of 2.56 using 2,4-dinitroaniline as indicator. No melting point was observed.

IR (cm$^{-1}$): 3553, 3336, 2944, 1651, 1686, 1518. $^1$H-NMR (400 MHz, d$_6$-DMSO): δ 1.45–1.66 (m, 6H), 2.378 (t, 2H), 3.104 (t, 2H), 8.26 (s, 1H), 11.98 (s, 1H). $^{13}$C-NMR (100 MHz, d$_6$-DMSO): δ 22.86, 29.15, 30.08, 35.42, 42.18, 179.25. FAB-MS for cation: m/z 114.1. C$_6$H$_{12}$BF$_4$NO (200.97): calcd: C, 35.83, H 5.97. Found: C, 35.92, H 5.84.

Example 3

Preparation of Caprolactam Chloroacetate

To a 100 ml flask containing 11.32 g of ε-caprolactam (0.1 mol), 30 ml benzene was added and stirred for dissolution. Then 9.45 g of chloroacetic acid (0.1 mol) in 20 ml benzene was added dropwise into the flask over 20 min at room temperature. Then the reaction was stirred for another 7 hours. Desired product was formed after benzene was removed under reduced pressure and dried at 110° C. under 1–5 mmHg for 1 hour. The yellowish, moisture- and water-stable liquid of caprolactam chloroacetate was obtained with a yield of 95.9%, which has an ionic conductivity of $2.9 \times 10^{-5}$ S/cm, a glass transition temperature of −67° C., and a Hammett acidic scale $H_0$ of 5.03 using methyl yellow as indicator. After several days, it changed into a yellowish solid with melting point of 29° C.

IR (cm$^{-1}$): 3287, 2937, 2861, 1728, 1623, 1441. $^1$H-NMR (400 MHz, D$_2$O): δ 1.35–1.52 (m, 3CH$_2$_), 2.22 (t, 2H), 2.99 (t, 2H), 4.01 (s, 2H). $^{13}$C-NMR (100 MHz, D$_2$O): δ 22.73, 28.56, 29.95, 35.62, 41.46, 42.54, 171.94, 182.72. FAB-MS for cation: m/z 114.2. C$_8$H$_{14}$NO$_3$Cl (207.5): calcd: C, 46.27, H 6.75. Found: C, 45.99, H 6.70.

Example 4

Preparation of Caprolactam Trifluoroacetate

To a 100 ml flask containing 11.32 g of ε-caprolactam (0.1 mol), 30 ml benzene was added and stirred for dissolution. 11.40 g of trifluoroacetic acid (0.1 mol) was added dropwise into the flask over 60 min at room temperature. Then the reaction was stirred for another 4 hours. Desired product was formed after benzene was removed under reduced pressure and dried at 110° C. under 1–5 mmHg for 1 hour. The colorless, moisture- and water-stable liquid of caprolactam trifluoroacetate was obtained with a yield of 97.5%, which has a glass transition temperature of −68.0° C., a density of 1.26 g/ml, a viscosity of 28 cP, an electrochemical window of 1.9 V, an ionic conductivity of $1.17 \times 10^{-4}$ S/cm, and a Hammett acidic scale $H_0$ of 4.54 using methyl yellow as indicator. No melting point was observed.

IR (cm$^{-1}$): 3238, 2944, 1777, 1658, 1169. $^1$H-NMR (400 MHz, CDCl$_3$): 1.65–1.82 (m, 6H), 2.51 (q, 2H), 3.27 (q, 2H), 8.06 (s, 1H), 15.89 (s, 1H). $^{13}$C-NMR (100 MHz, CDCl$_3$): 22.74, 28.86, 30.25, 35.76, 42.83, 115.23 (q, CF$_3$), 160.99, 181.02. FAB-MS for cation: m/z 114.1. C$_8$H$_{12}$F$_3$NO$_3$ (227.1): calcd: C, 42.27, H 5.28. Found: C, 42.31, H 5.20.

Example 5

Preparation of Caprolactam Nitrate

To a 100 ml flask containing 11.32 g of ε-caprolactam (0.1 mol), 30 ml water was added and stirred for dissolution. 9.69 g of 65% nitric acid (0.1 mol) was added dropwise into the flask over 30 min at room temperature. Then the reaction was stirred for another 8 hours. Desired product was formed after water was removed under reduced pressure and dried at 110° C. under 1–5 mmHg for 1 hour. The white, moisture- and water-stable solid of caprolactam nitrate was obtained with a yield of 98.1%, which has a melting point of 40–42° C. No glass transition temperature was observed.

IR (cm$^{-1}$): 3551, 3334, 2943, 1685, 1652, 1516. $^1$H-NMR (400 MHz, CDCl$_3$): 1.65–1.82 (m, 6H), 2.57 (t, 2H), 3.35 (d,

2H), 8.38 (s, 1H). $^{13}$C-NMR (100 MHz, CDCl$_3$): 22.61, 29.04, 30.16, 35.69, 42.91, 179.27. FAB-MS for cation: m/z 114.2. C$_6$H$_{12}$N$_2$O$_4$ (176.0): calcd: C, 40.91, H 6.82. Found: C, 40.78, H 6.73.

Example 6

Preparation of 4-Methylpyrrolidonium Trifluoroacetate

To a 100 ml flask containing 9.91 g of 4-methylpyrrolidone (0.1 mol), 30 ml benzene was added and stirred for dissolution. 11.40 g of trifluoroacetic acid (0.1 mol) was added dropwise into the flask over 40 min at room temperature. Then the reaction was stirred for another 6 hours. Desired product was formed after benzene was removed under reduced pressure and dried at 110° C. under 1–5 mmHg for 1 hour. The brown viscous, moisture- and water-stable liquid of 4-methylpyrrolidonium trifluoroacetate was obtained with a yield of 97.7%, which has a glass transition temperature of –85.0° C., a density of 1.33 g/ml, a viscosity of 22 cP, an electrochemical window of 2.4 V, an ionic conductivity of 5.63×10$^{-4}$ S/cm, and a Hammett acidic scale H$_0$ of 4.82 using methyl yellow as indicator. No melting point was observed.

IR (cm$^{-1}$): 3251, 2956, 2887, 1687, 1292. $^1$H-NMR (400 MHz, CDCl$_3$): 1.52 (d, 3H), 2.11–2.19 (m, 2H), 2.45 (q, 1H), 3.49 (t, 2H), 7.72(s, 1H). $^{13}$C-NMR (100 MHz, CDCl$_3$): 18.74, 25.63, 30.42, 37.05, 115.16 (q, CF$_3$), 163.74, 181.41. FAB-MS for cation: m/z 100.1. C$_7$H$_{10}$F$_3$NO$_3$ (162.1): calcd: C, 51.82, H 6.17. Found: C, 51.74, H 6.05.

Example 7

Preparation of Octanolactam Tetrafluoroborate

To a 100 ml flask containing 14.12 g of octanolactam (0.1 mol), 30 ml water was added and stirred for dissolution. 21.95 g 40 wt % aqueous solution of tetrafluoroboric acid (0.1 mol) was added dropwise into the flask over 20 min at room temperature. Then the reaction was stirred for another 1 hour. Desired product was formed after water was removed under reduced pressure and dried at 110° C. under 1–5 mmHg for 1 hour. The colorless, slightly viscous, moisture- and water-stable liquid of octanolactam tetrafluoroborate was obtained with a yield of 96.7%, which has a glass transition temperature of –61.0° C., a density of 1.36 g/ml, a viscosity of 524 cP, an electrochemical window of 2.0 V, an ionic conductivity of 1.04×10$^{-4}$ S/cm, and a Hammett acidic scale H$_0$ of 1.32 using methyl yellow as indicator. No melting point was observed.

IR (cm$^{-1}$): 3248, 2963, 2894, 1663, 1285. $^1$H-NMR (400 MHz, d$_6$-DMSO) δ 1.47–1.71 (m, 12H), 2.17 (t, 2H), 3.06 (t, 2H), 8.02 (s, 1H), 11.72 (s, 1H). $^{13}$C-NMR (100 MHz, d$_6$-DMSO): δ 22.86, 24.53, 28.61, 29.15, 30.08, 35.42, 42.18, 174.38. FAB-MS for cation: m/z 142.2. C$_8$H$_{16}$BF$_4$NO (228.8): calcd: C, 41.96, H 6.99. Found: C, 41.85, H 6.87.

Example 8

Preparation of Octanolactam Trifluoroacetate

To a 100 ml flask containing 14.12 g of octanolactam (0.1 mol), 30 ml benzene was added and stirred for dissolution. 11.40 g of trifluoroacetic acid (0.1 mol) was added dropwise into the flask over 30 min at room temperature. Then the reaction was stirred for another 4 hours. Desired product was formed after benzene was removed under reduced pressure and dried at 110° C. under 1–5 mmHg for 1 hour. The colorless, slightly viscous, moisture- and water-stable liquid of octanolactam trifluoroacetate was obtained with a yield of 98.2%, which has a glass transition temperature of –64° C., a density of 1.27 g/ml, a viscosity of 62 cP, an electrochemical window of 2.1 V, an ionic conductivity of 2.57×10$^{-4}$ S/cm, and a Hammett acidic scale H$_0$ of 4.79 using methyl yellow as indicator. No melting point was observed.

IR (cm$^{-1}$): 3246, 2965, 2891, 1662, 1283. $^1$H-NMR (400 MHz, d$_6$-DMSO): δ 1.45–1.68 (m, 12H), 2.14 (t, 2H), 2.97 (t, 2H), 8.10 (s, 1H), 15.76 (s, 1H). $^{13}$C-NMR (100 MHz, d$_6$-DMSO): δ 22.71, 24.46, 29.32, 30.08, 31.65, 35.42, 42.18, 117.36 (q, CF$_3$), 164.68, 178.35. FAB-MS for cation: m/z 142.2. C$_{10}$H$_{16}$F$_3$NO$_3$ (255.0): calcd: C, 47.06, H 6.27. Found: C, 46.91, H 6.15.

Example 9

Preparation of Caprolactam Hydrosulfate

To a 100 ml flask containing 11.32 g of caprolactam (0.1 mol), 30 ml benzene was added and stirred for dissolution. Then 9.80 g of concentrated sulfuric acid (0.1 mol) was added dropwise into the flask over 30 min at room temperature. Then the reaction was stirred for another 5 hours. Desired product was formed after benzene was removed under reduced pressure and dried at 110° C. under 1–5 mmHg for 1 hour. The colorless, slightly viscous, moisture- and water-stable liquid of caprolactam hydrosulfate was obtained with a yield of 98.2%. It changed into a wax-like solid after several days with melting point of 25–28° C. No glass transition temperature was observed.

IR (cm$^{-1}$): 3549, 3334, 2942, 1684, 1652. $^1$H-NMR (400 MHz, CDCl$_3$): 1.62–1.78 (m, 6H), 2.52 (t, 2H), 3.41 (d, 2H), 8.43 (s, 1H). $^{13}$C-NMR (100 MHz, CDCl$_3$): 21.89, 28.74, 30.07, 35.68, 43.25, 179.27. FAB-MS for cation: m/z 114.2. C$_6$H$_{13}$NO$_5$S (211.0): calcd: C, 34.12, H 6.16. Found: C, 33.95, H 6.04.

Example 10

Preparation of Caprolactam Dihydrogen Phosphate

To a 100 ml flask containing 11.32 g of caprolactam (0.1 mol), 30 ml water was added and stirred for dissolution. 11.53 g of 85% phosphoric acid (0.1 mol) was added dropwise into the flask over 30 min at room temperature. Then the reaction was stirred for another 12 hours. Desired product was formed after water was removed under reduced pressure and dried at 110° C. under 1–5 mmHg for 1 hour. The white, moisture- and water-stable solid of caprolactam dihydrogen phosphate was obtained with a yield of 98.6% and a melting point of 61–64° C. No glass transition temperature was observed.

IR (cm$^{-1}$): 3556, 3340, 2944, 1685, 1650, 1516. $^1$H-NMR (400 MHz, CDCl$_3$): 1.59–1.74 (m, 6H), 2.47 (t, 2H), 3.52 (d, 2H), 8.35 (s, 1H). $^{13}$C-NMR (100 MHz, CDCl$_3$): 21.65, 27.83, 30.28, 35.37, 43.61, 180.42. FAB-MS for cation: m/z 114.2. C$_6$H$_{14}$NO$_5$P (211.0): calcd: C, 34.12, H 6.64. Found: C, 34.08, H 6.55.

Example 11

Large-scale Preparation of Caprolactam Tetrafluoroborate

The procedure is the same as in example 2 except that the amount of ε-caprolactam and tetrafluoroboric acid added is increased to 1 mol respectively. Desired product of caprolactam tetrafluoroborate was obtained with a yield of 96.3%. No melting point was observed. The density, the viscosity, the ionic conductivity, the glass transition temperature, and the Hammett acidic scale $H_0$ are the same as those of in example 2.

IR (cm$^{-1}$): 3551, 3339, 2943, 1685, 1650, 1517. $^1$H-NMR (400 MHz, d$_6$-DMSO): δ 1.44–1.63 (m, 6H), 2.35 (t, 2H), 3.08 (t, 2H), 8.27 (s, 1H), 11.95 (s, 1H). $^{13}$C-NMR (100 MHz, d$_6$-DMSO): δ 22.82, 29.16, 30.10, 35.43, 42.15, 179.41. FAB-MS for cation: m/z 114.1. C$_6$H$_{12}$BF$_4$NO (200.97): calcd: C, 35.83, H 5.97. Found: C, 35.77, H 5.86.

What is claimed is:

1. A Brønsted acidic room temperature ionic liquid having a lactam as the cation group, represented by a general formula (I),

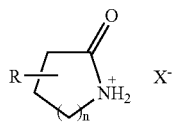

(I)

wherein R represents a hydrogen atom or an alkyl group from 1 to 4 carbon atoms, n is 1 to 5, and X$^-$ represents the anion group of Brønsted acid HX.

2. The Brønsted acidic room temperature ionic liquid according to claim 1, wherein R is selected from the group consisting of methyl, ethyl, n-propyl, i-propyl, n-butyl, i-butyl, and hydrogen atom.

3. The Brønsted acidic room temperature ionic liquid according to claim 1, wherein X$^-$ is selected from the group consisting of BF$_4^-$, CF$_3$SO$_3^-$, CF$_3$COO$^-$, CH$_3$COO$^-$, ClCH$_2$COO$^-$, C$_6$H$_5$COO$^-$, C$_6$H$_5$CH$_2$COO$^-$, NO$_3^-$, HSO$_4^-$, H$_2$PO$_4^-$, (CN)$_2$N$^-$, and CH$_3$SO$_3^-$.

4. A method for preparing a Brønsted acidic room temperature ionic liquid having a lactam as the cation group, represented by a general formula (I),

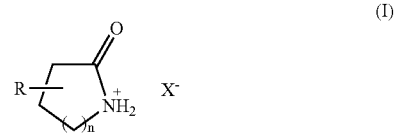

(I)

wherein R represents a hydrogen atom or an alkyl group containing 1 to 4 carbon atoms, n is 1 to 5, and X$^-$ represents the anion group of Brønsted acid HX, characterized by reacting a lactam compound represented by a general formula (II),

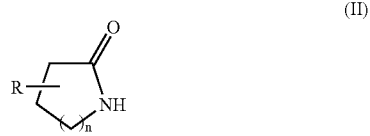

(II)

wherein R represents a hydrogen atom or an alkyl group from 1 to 4 carbon atoms, and n is 1 to 5, with a Brønsted acid HX at room temperature, in the presence of a reaction medium selected from the group consisting of benzene, toluene, ethyl ether, cyclohexane, water and a mixture thereof.

5. The method according to claim 4, wherein the molar ratio of the lactam compound to the Brønsted acid is 1:1.

6. The method according to claim 4, wherein the Brønsted acid is selected from the group consisting of tetrafluoroboric acid, trifluoromethanesulfonic acid, trifluoroacetic acid, acetic acid, chloroacetic acid, benzoic acid, phenylacetic acid, nitric acid, Sulfuric acid, phosphoric acid, dicyanoimide and methanesulfonic acid.

* * * * *